(12) United States Patent
Lu et al.

(10) Patent No.: US 8,809,444 B2
(45) Date of Patent: *Aug. 19, 2014

(54) NETWORK COPOLYMER CROSSLINKED EMULSIONS AND DEMULSIFYING COMPOSITIONS COMPRISING THE SAME

(75) Inventors: Ning Lu, Chappaqua, NY (US);
Sigfredo Gonzalez, Danbury, CT (US);
Ernie M. Silvestre, Yonkers, NY (US);
Geng Wang, Vienna, WV (US)

(73) Assignee: Momentive Performance Materials Inc., Waterford, NY (US)

( * ) Notice: Subject to any disclaimer, the term of this patent is extended or adjusted under 35 U.S.C. 154(b) by 774 days.

This patent is subject to a terminal disclaimer.

(21) Appl. No.: 12/646,364

(22) Filed: Dec. 23, 2009

(65) Prior Publication Data
US 2011/0152423 A1    Jun. 23, 2011

(51) Int. Cl.
*C08K 5/541* (2006.01)

(52) U.S. Cl.
USPC .................................. 524/547; 524/261

(58) Field of Classification Search
USPC ........... 524/547, 609, 801; 528/398; 526/286, 526/287, 289
See application file for complete search history.

(56) References Cited

U.S. PATENT DOCUMENTS

| | | | | |
|---|---|---|---|---|
| 2002/0052459 | A1* | 5/2002 | Kohlhammer et al. ....... | 526/287 |
| 2003/0144399 | A1* | 7/2003 | Matta et al. .................. | 524/419 |
| 2008/0281038 | A1* | 11/2008 | Takahashi et al. ............ | 524/602 |

FOREIGN PATENT DOCUMENTS

| | | |
|---|---|---|
| EP | 1800686 | 6/2007 |
| JP | 10-338709 A | 12/1998 |

OTHER PUBLICATIONS

Wu, Shaobing et al., "Effects of sulphonic and phosphonic acrylic monomers on the crosslinking of acrylic latexes with cycloaliphatic epoxide" Progress in Organic Coatings 36 (1-2) 21-33 Coden: POGCAT; ISSN: 0300-9440, 1999, XP002649727.

Wang D et al., "Synthesis and characterization of a novel degradable phosphate-containing hydrogel", Biomaterials, Elsevier Science Publishers BV., Barking, GB, vol. 24, No. 22, Oct. 1, 2003, pp. 3969-3980, XP004434239.

Miyata, Takashi et al., "Stimuli-sensitives of hydrogels containing phosphate groups", Macromol. Chem. Phys. 195(4), 1111-20 Coden: MCHPES: ISSN: 1022-1352, 1994 XP002649726.

* cited by examiner

*Primary Examiner* — Doris Lee
(74) *Attorney, Agent, or Firm* — Dominick G. Vicari; Joseph S. Ostroff

(57) ABSTRACT

The present invention is directed to a network composition the reaction product of: (i) at least one anionic polymerizable ethylenically unsaturated monomer (I) selected from the group consisting of

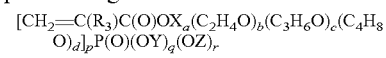

where
$R_3$=H or alkyl of 1 to about 6 carbon atoms;
X=alkyl, aryl, or alkaryl diradical connecting group of 0 to about 9 carbon atoms; a is 0 to about 100; b is 0 to about 100; c is 0 to about 100; d is 0 to about 100; q is 0 to about 2; r is 0 to about 2; p is 1 to about 3 subject to the limitation that p+q+r=3; and Y and Z is H, or metal ion; and

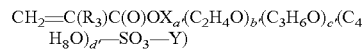

where $R_3$=H or alkyl of from 1 to about 6 carbon atoms;
X=alkyl, aryl, or alkaryl diradical connecting group of 0 to about 9 carbon atoms;
a' is 0 to about 100; b' is 0 to about 100; c' is 0 to about 100; d' is 0 to about 100; Y is H, or metal ion; and
(ii) one or more additional monomers (II) selected from the group consisting of acrylic acid/acrylate, methacrylic acid/methacrylate, acrylamides, vinyl acetate and styrene, which are copolymerizable with (I); and
(iii) a cross-linking agent (III), capable of copolymerizing with (I) and (II).

6 Claims, No Drawings

NETWORK COPOLYMER CROSSLINKED EMULSIONS AND DEMULSIFYING COMPOSITIONS COMPRISING THE SAME

FIELD OF THE INVENTION

The present invention relates to network copolymer emulsions compositions and products comprising the same.

BACKGROUND OF THE INVENTION

Network copolymer emulsion compositions can exhibit a variety of physical properties. The polymers can be modified to be hydrophilic, lipophilic and hydrophobic depending on the nature of the organic substituents. Emulsions comprising network copolymer compositions made by simultaneously polymerizing and cross-linking, in the presence of a free radical polymerization catalyst, a mixture of polymerizable ethylenically unsaturated monomers having particular structures have utility in a variety of applications including personal care (hair conditioners, skin care and color cosmetics), textile treatments, hard surface modifiers, agricultural adjuncts, and the like. These emulsions are further described and claimed below as well as methods of making the emulsions.

SUMMARY OF THE INVENTION

According to the invention there is provided an emulsion comprising a continuous and a discontinuous phase wherein the discontinuous phase comprises water and the continuous phase comprises a network copolymer composition comprising a reaction product of:
i) at least one anionic polymerizable ethylenically unsaturated monomer (I) selected from the group consisting of

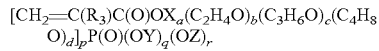

where
$R_3$=H or alkyl of 1 to about 6 carbon atoms;
X=alkyl, aryl, or alkaryl diradical connecting group of 0 to about 9 carbon atoms; a is 0 to about 100;
b is 0 to about 100;
c is 0 to about 100;
d is 0 to about 100;
q is 0 to about 2;
r is 0 to about 2;
p is 1 to about 3 subject to the limitation that p+q+r=3; and
Y and Z is H, or metal ion;
and

where
$R_3$=H or alkyl of from 1 to about 6 carbon atoms;
X=alkyl, aryl, or alkaryl diradical connecting group of 0 to about 9 carbon atoms;
a' is 0 to about 100;
b' is 0 to about 100;
c' is 0 to about 100;
d' is 0 to about 100;
Y is H, or metal ion; and
(ii) one or more additional monomers (II) selected from the group consisting of acrylic acid/acrylate, methacrylic acid/methacrylate, acrylamides, vinyl acetate and styrene, which are copolymerizable with (I); and
(iii) a cross-linking agent (III), capable of copolymerizing with (I) and (II).

The emulsions of the present invention can either be aqueous or non-aqueous and can have the network composition in either the continuous or discontinuous phase of the emulsion. The present invention is also directed to a demulsifying composition comprising the emulsions of the present invention.

Additional embodiments are also part of the present invention, which are further described in the Detailed Description of the Invention below.

DETAILED DESCRIPTION OF THE INVENTION

The present invention is directed to network compositions of the present invention utilized as prepared or as the main component in emulsions. As is generally known, emulsions comprise at least two immiscible phases one of which is continuous and the other which is discontinuous. One of the immiscible liquids in an emulsion is generally polar, and often water based and the other liquid is generally non-polar, generally defined as an oil phase. Further emulsions may be liquids with varying viscosities or solids. Emulsions may also contain gases as well as solids. Additionally the particle size of the emulsions may be render them microemulsions and when sufficiently small microemulsions may be transparent. Further it is also possible to prepare emulsions of emulsions and these are generally known as multiple emulsions. These emulsions may be:

1) aqueous emulsions where the discontinuous phase comprises water and the continuous phase comprises the copolymer network of the present invention;

2) aqueous emulsions where the discontinuous phase comprises the copolymer network of the present invention and the continuous phase comprises water;

3) non-aqueous emulsions where the discontinuous phase comprises a non-aqueous hydroxylic solvent and the continuous phase comprises the copolymer network of the present invention; and 4) non-aqueous emulsions where the continuous phase comprises a non-aqueous hydroxylic organic solvent and the discontinuous phase comprises the copolymer network of the present invention.

Non-aqueous emulsions comprising a silicone phase are described in U.S. Pat. No. 6,060,546 the contents of which are incorporated herein in its entirety by reference.

According to the present invention there is provided an emulsion comprising a continuous and a discontinuous phase wherein the continuous phase comprises water and the discontinuous phase comprises a network copolymer composition comprising a reaction product of:
i) at least one anionic polymerizable ethylenically unsaturated monomer (I) selected from the group consisting of

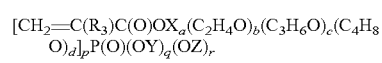

where
$R_3$=H or alkyl of 1 to about 6 carbon atoms;
X=alkyl, aryl, or alkaryl diradical connecting group of 0 to about 9 carbon atoms; a is 0 to about 100, 1 to about 100, preferably 0 to about 40 and more preferably about 0 to about 15;
b is 0 to about 100, 1 to about 100, preferably 0 to about 40 and more preferably about 0 to about 15;
c is 0 to about 100, 1 to about 100, preferably 0 to about 40 and more preferably about 0 to about 15;
d is 0 to about 100, 1 to about 100, preferably 0 to about 40 and more preferably about 0 to about 15;
q is 0 to about 2;
r is 0 to about 2;

p is 1 to about 3 subject to the limitation that p+q+r=3; and
Y and Z is H, or metal ion;
and

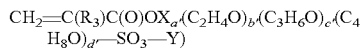

where
$R_3$=H or alkyl of from 1 to about 6 carbon atoms;
X=alkyl, aryl, or alkaryl diradical connecting group of 0 to about 9 carbon atoms;
a' is 0 to about 100, 1 to about 100, preferably 0 to about 40 and more preferably about 0 to about 15;
b' is 0 to about 100, 1 to about 100, preferably 0 to about 40 and more preferably about 0 to about 15;
c' is 0 to about 100, 1 to about 100, preferably 0 to about 40 and more preferably about 0 to about 15;
d' is 0 to about 100, 1 to about 100, preferably 0 to about 40 and more preferably about 0 to about 15;
Y is H, or metal ion; and
(ii) one or more additional monomers (II) selected from the group consisting of acrylic acid/acrylate, methacrylic acid/methacrylate, acrylamides, vinyl acetate and styrene, which are copolymerizable with (I); and
(iii) a cross-linking agent (III), capable of copolymerizing with (I) and (II).

In one embodiment of the present invention the cross-linked components of the emulsions includes up to about 0.5 to about 50 percent by weight of the total weight of monomers, of one or more additional monomer, preferable any acrylic acid/acrylate, methacrylic acid/methacrylate, or monomers such as acrylamides, vinyl acetate and styrene, which are copolymerizable with (i). Any organic acrylate or methacrylate can be employed as the co-monomers in the composition. Examples of such monomers include, but are not limited to, acrylic acid and methacrylic acid or the derivatives such as methyl, ethyl, butyl, amyl, 2-ethylhexyl, cyclohexyl, vinyl, ally, hydroxyethyl, perfluoroethyl, isobornyl, phenoxyethyl, tetraethylene glycol, tripropylene glycol, trimethylolpropane, polyoxyalkylene.

According to another aspect of the present invention there is provided an aqueous emulsion having a continuous and a discontinuous phase is provided wherein the discontinuous phase comprises water and the continuous phase comprises a network composition comprising the reaction product of:
i) at least one anionic polymerizable ethylenically unsaturated monomer (I) selected from the group consisting of

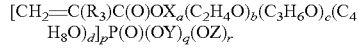

where
$R_3$=H or alkyl of 1 to about 6 carbon atoms;
X=alkyl, aryl, or alkaryl diradical connecting group of 0 to about 9 carbon atoms; a is 0 to about 100, 1 to about 100, preferably 0 to about 40 and more preferably about 0 to about 15;
b is 0 to about 100, 1 to about 100, preferably 0 to about 40 and more preferably about 0 to about 15;
c is 0 to about 100, 1 to about 100, preferably 0 to about 40 and more preferably about 0 to about 15;
d is 0 to about 100, 1 to about 100, preferably 0 to about 40 and more preferably about 0 to about 15;
q is 0 to about 2;
r is 0 to about 2;
p is 1 to about 3 subject to the limitation that p+q+r=3; and
Y and Z is H, or metal ion;
and

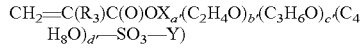

where
$R_3$=H or alkyl of from 1 to about 6 carbon atoms;
X=alkyl, aryl, or alkaryl diradical connecting group of 0 to about 9 carbon atoms;
a' is 0 to about 100, 1 to about 100, preferably 0 to about 40 and more preferably about 0 to about 15;
b' is 0 to about 100, 1 to about 100, preferably 0 to about 40 and more preferably about 0 to about 15;
c' is 0 to about 100, 1 to about 100, preferably 0 to about 40 and more preferably about 0 to about 15;
d' is 0 to about 100, 1 to about 100, preferably 0 to about 40 and more preferably about 0 to about 15;
Y is H, or metal ion; and
(ii) one or more additional monomers (II) selected from the group consisting of acrylic acid/acrylate, methacrylic acid/methacrylate, acrylamides, vinyl acetate and styrene, which are copolymerizable with (I); and
(iii) a cross-linking agent (III), capable of copolymerizing with (I) and (II).

Yet another aspect of the present invention is directed to a non-aqueous emulsion comprising a continuous and a discontinuous phase wherein the continuous phase comprises non-aqueous hydroxylic organic solvent and the discontinuous phase comprises a network copolymer composition comprising a reaction product of:
i) at least one anionic polymerizable ethylenically unsaturated monomer (I) selected from the group consisting of

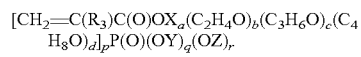

where
$R_3$=H or alkyl of 1 to about 6 carbon atoms;
X=alkyl, aryl, or alkaryl diradical connecting group of 0 to about 9 carbon atoms; a is 0 to about 100, 1 to about 100, preferably 0 to about 40 and more preferably about 0 to about 15;
b is 0 to about 100, 1 to about 100, preferably 0 to about 40 and more preferably about 0 to about 15;
c is 0 to about 100, 1 to about 100, preferably 0 to about 40 and more preferably about 0 to about 15;
d is 0 to about 100, 1 to about 100, preferably 0 to about 40 and more preferably about 0 to about 15;
q is 0 to about 2;
r is 0 to about 2;
p is 1 to about 3 subject to the limitation that p+q+r=3; and
Y and Z is H, or metal ion;
and

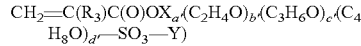

where
$R_3$=H or alkyl of from 1 to about 6 carbon atoms;
X=alkyl, aryl, or alkaryl diradical connecting group of 0 to about 9 carbon atoms;
a' is 0 to about 100, 1 to about 100, preferably 0 to about 40 and more preferably about 0 to about 15;
b' is 0 to about 100, 1 to about 100, preferably 0 to about 40 and more preferably about 0 to about 15;
c' is 0 to about 100, 1 to about 100, preferably 0 to about 40 and more preferably about 0 to about 15;
d' is 0 to about 100, 1 to about 100, preferably 0 to about 40 and more preferably about 0 to about 15;
Y is H, or metal ion; and
(ii) one or more additional monomers (II) selected from the group consisting of acrylic acid/acrylate, methacrylic acid/methacrylate, acrylamides, vinyl acetate and styrene, which are copolymerizable with (I); and (iii) a cross-linking agent (III), capable of copolymerizing with (I) and (II).

Still yet another aspect of the present invention is directed to a non-aqueous emulsion having a continuous and a discontinuous phase wherein the discontinuous phase comprises non-aqueous hydroxylic organic solvent and the continuous phase comprises a network composition comprising the reaction product of:

i) at least one anionic polymerizable ethylenically unsaturated monomer (I) selected from the group consisting of

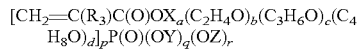

where $R_3$=H or alkyl of 1 to about 6 carbon atoms;

X=alkyl, aryl, or alkaryl diradical connecting group of 0 to about 9 carbon atoms; a is 0 to about 100, 1 to about 100, preferably 0 to about 40 and more preferably about 0 to about 15;

b is 0 to about 100, 1 to about 100, preferably 0 to about 40 and more preferably about 0 to about 15;

c is 0 to about 100, 1 to about 100, preferably 0 to about 40 and more preferably about 0 to about 15;

d is 0 to about 100, 1 to about 100, preferably 0 to about 40 and more preferably about 0 to about 15;

q is 0 to about 2;

r is 0 to about 2;

p is 1 to about 3 subject to the limitation that p+q+r=3; and Y and Z is H, or metal ion;

and

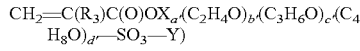

where $R_3$=H or alkyl of from 1 to about 6 carbon atoms;

X=alkyl, aryl, or alkaryl diradical connecting group of 0 to about 9 carbon atoms;

a' is 0 to about 100, 1 to about 100, preferably 0 to about 40 and more preferably about 0 to about 15;

b' is 0 to about 100, 1 to about 100, preferably 0 to about 40 and more preferably about 0 to about 15;

c' is 0 to about 100, 1 to about 100, preferably 0 to about 40 and more preferably about 0 to about 15;

d' is 0 to about 100, 1 to about 100, preferably 0 to about 40 and more preferably about 0 to about 15;

Y is H, or metal ion; and (ii) one or more additional monomers (II) selected from the group consisting of acrylic acid/acrylate, methacrylic acid/methacrylate, acrylamides, vinyl acetate and styrene, which are copolymerizable with (I); and (iii) a cross-linking agent (III), capable of copolymerizing with (I) and (II).

The emulsions of the present invention can be, for example, a water-in-oil, an oil-in-water emulsion or a multiple phase emulsion. The emulsions particularly considered herein are those wherein the emulsified component is in the form of droplets with droplet sizes in the range of about 0.1 microns up to about 200 microns, more typically about 1-100 microns. The emulsified component can be unstabilized, but is more typically stabilized by a stabilizing amount of a surfactant and/or dispersed particulate solid. Further it is also possible to prepare emulsions of emulsions and these are generally known as multiple emulsions.

The aqueous phase can be essentially pure water, or alternatively, water with varying amounts of solid (particulate) materials, salt or other chemicals.

The oil phase is any hydrophobic phase substantially insoluble with the aqueous phase. For example, the oil phase can be composed of one or more hydrophobic chemicals, typically liquids, which individually or in combination are mainly insoluble in the aqueous phase. Such hydrophobic chemicals can be, for example, linear or branched, cyclic or acyclic, saturated or unsaturated, aliphatic or aromatic hydrocarbons. The hydrocarbons typically contain at least six carbon atoms and can be unsubstituted, or alternatively, substituted with one or more heteroatom-containing group (e.g., hydroxyl, amino, carboxyl, amide, anhydride, ester, or ether groups) as long as the hydrocarbons remain mainly insoluble with the aqueous phase.

The cross-linking agent in any of the above-described emulsions above can be a polyfunctional vinylidene monomer containing at least two unsaturated groups. Examples of polyfunctional vinylidene monomers of the network composition is selected from the group consisting of butadiene, isoprene, divinyl benzene, allyl acrylates, polyalkylene glycol diacrylates and dimethacrylates. Other crosslinking agents include diallyl esters and dimethallyl esters and other crosslinking agents listed and described in U.S. Pat. No. 4,509,949 herein incorporated in its entirety by reference.

The network composition of any of the above-described emulsions comprises about 40 to about 99, preferably 50 to about 85, more preferably about 60 to about 75 weight percent based on the total weight of the monomers of at least one anionic polymerizable ethylenically unsaturated monomer (I), about 0.5 to about 50, preferably about 5 to about 40, more preferably about 10 to about 30 weight percent based on the total weight of the monomers of the additional monomers and about 0.1 to about 10, preferably about 2 to about 8, more preferably about 3 to about 6 weight percent based on the total weight of the monomers of said cross-linking agent.

Both the acrylate cross-links and the polyether substituents of the networked compositions of the emulsions are capable of hydrogen bonding with water and other hydroxylic solvents, increasing content of either, all other composition variables remaining constant, will tend to increase the water swellability of the resulting cross-linked network polymer. Because it is possible to vary the compositional parameters of the cross-linked network copolymers of the invention in an almost limitless fashion, some compositions are both water swellable and oil swellable while others are only water swellable or oil swellable, and some compositions will not be swellable with any of the solvents discussed herein. The amount of crosslinking present in the crosslinked network may be characterized with respect to the degree of swelling exhibited by the network in the fluid.

The cross-linked structure of the network composition of the emulsions of the present invention is effective to allow the network to be swollen from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid component from the silicone composition of the present invention to leave the original volume, that is, the volume of the copolymer network in the absence of the fluid.

According to yet another aspect of the present invention, the network compositions of the aqueous emulsions comprises a reaction product of monomer (I), as provided below, wherein the subscript p is equal to 2 or 3 and monomer (I) acts as the cross linking agent. In other words, no additional cross linking agent is necessary. That is, the present invention is directed to an emulsion comprising a network composition having at least one anionic polymerizable ethylenically unsaturated monomer (I)

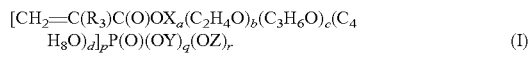

(I)

where

R$_3$=H or alkyl of 1 to about 6 carbon atoms;

X=alkyl, aryl, or alkaryl diradical connecting group of 0 to about 9 carbon atoms; a is 0 to about 100, 1 to about 100, preferably 0 to about 40 and more preferably about 0 to about 15;

b is 0 to about 100, 1 to about 100, preferably 0 to about 40 and more preferably about 0 to about 15;

c is 0 to about 100, 1 to about 100, preferably 0 to about 40 and more preferably about 0 to about 15;

d is 0 to about 100, 1 to about 100, preferably 0 to about 40 and more preferably about 0 to about 15;

q is 0 to about 2, 1 to about 100, preferably 0 to about 40 and more preferably about 0 to about 15;

r is 2 or 3;

p is 1 to about 3 subject to the limitation that p+q+r=3; and

Y and Z is H, or metal ion; and (ii) one or more additional monomers (II) selected from the group consisting of acrylic acid/acrylate, methacrylic acid/methacrylate, acrylamides, vinyl acetate and styrene, which are copolymerizable with (I). No additional crosslinking agent is necessary for the reaction of monomer (I) and monomer (II) in this embodiment of the present invention since monomer (I) having a p value of 2 or 3 is essentially a polyunsaturated molecule having 2 or 3 double bonds and therefore acts as a cross-linking agent.

The present invention is also directed to an aqueous or non-aqueous emulsions comprising the network composition described directly above in either the continuous or discontinuous phases of the emulsions. In the aqueous emulsions of the present invention where the network composition is in the discontinuous phase, the continuous phase comprises water. In the aqueous emulsions of the present invention where the network composition is in the continuous phase, the discontinuous phase comprises water.

In the non-aqueous emulsions of the present invention where the network composition is in the discontinuous phase, the continuous phase comprises non-aqueous hydroxylic organic solvent. In the non-aqueous emulsions of the present invention where the network composition is in the continuous phase, the discontinuous phase comprises non-aqueous hydroxylic organic solvent.

The aqueous emulsions of the present invention typically have a creamy consistency, wherein the copolymer network acts as a means for gelling the fluid to reversibly impart characteristics of a solid to the fluid. At rest, the aqueous emulsion comprising the composition exhibits the properties of a solid gel material. The aqueous emulsions comprising the network composition of the present invention exhibits high stability and resistance to syneresis, that is, the composition exhibits little or no tendency for fluid to flow from the composition and imparts high stability and syneresis resistance to personal care compositions, which include the composition as a component. The high stability and syneresis resistance persists with prolonged aging of such silicone compositions and personal care compositions. However, fluid may be released from the network by subjecting the composition to a shearing force, such as, for example, by rubbing the composition between one's fingers, to provide improved sensory feel characteristic of the fluid component of the material.

Water (or a water equivalent such as a non-aqueous hydroxylic solvent), siloxane, linear or cyclic, or lipophilic fluid (oil swelling agent, oil swellable) may be used as the swelling agent. Lipophilic fluids suitable for use as the fluid component of the composition of the present invention are those compounds or mixtures of two or more compounds that are in the liquid state at or near room temperature, for example, from about 20° C. about 50° C., and about one atmosphere pressure, and include, for example, silicone fluids, hydrocarbon fluids, esters, alcohols, fatty alcohols, glycols and organic oils. In a preferred embodiment, the fluid component of the composition of the present invention exhibits a viscosity of below about 1,000 cSt, preferably below about 500 cSt, more preferably below about 250 cSt, and most preferably below 100 cSt, at 25° C.

In another embodiment of the present invention, the copolymer network is a crosslinked network that is insoluble in various fluid components, but that is capable of being swollen by the fluid. The amount of crosslinking present in the crosslinked network may be characterized with respect to the degree of swelling exhibited by the network in the fluid. In another preferred embodiment, the crosslinked structure of the network is effective to allow the network to be swollen by water, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid components from the composition of the present invention to leave the original volume, that is, the volume of the copolymer network in the absence of the fluid. In another preferred embodiment, the crosslinked structure of the network is effective to allow the network to be swollen by a lipophilic fluid, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid components from the composition of the present invention to leave the original volume, that is, the volume of the copolymer network in the absence of the fluid.

In yet another preferred embodiment of the present invention, the cross linked structure of the network composition is effective to allow the network to be swollen by a low molecular weight silicone fluid, such as, for example, decamethylcyclopentasiloxane, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid component from the composition of the present invention to leave the original volume, that is, the volume of the copolymer network in the absence of the fluid.

The fluid component of the network composition of the emulsions of the present invention can comprise an emollient compound. Suitable emollient compounds include any fluid that provides emollient properties, that is, that when applied to skin, tend to remain on the surface of the skin or in the stratum corneum layer of the skin to act as lubricants, reduce flaking and to improve the appearance of the skin. Emollient compound are generically known and include, for example, hydrocarbons, such as for example, isododecane, isohexadecane and hydrogenated polyisobutene, organic waxes, such as for example, jojoba, silicone fluids, such as, for example, cyclopentasiloxane, dimethicone and bis-phenylpropyl dimethicone, esters, such as, for example, octyldodecyl neopentanoate and coleyl oleate, as well as fatty acids and alcohols, such as for example, oleyl alcohol and isomyristyl alcohol.

Yet another aspect of the present invention is directed to an aqueous or non-aqueous emulsions comprising the network composition comprising the reaction product of at least one anionic polymerizable ethylenically unsaturated monomer (I) selected from the group consisting of $CH_2$=$C(CH_3)C(O)$ $O(C_3H_6O)_6P(O)(OH)(ONa)$, $CH_2$=$C(CH_3)C(O)O(C_3H_6O)_6P(O)(OH)_2$, $CH_2$=$CHC(O)O(C_3H_6O)_6P(O)(OH)(OH)_2$, and $CH_2$=$C(CH_3)C(O)O(C_2H_4O)_nP(O)(OH)_2$ and combinations thereof;

additional monomers (II) selected from the group consisting of: $CH_2$=$CHC(O)OH$ and $CH_2$=$C(CH_3)C(O)O(C_3H_6O)_6H$ and combinations thereof; and cross-linking agent (III) selected from the group consisting of $CH_2$=$CHC(O)O(C_2H_4O)_nC(O)OCH$=$CH_2)$, $CH_2$=$C(CH_3)CO_2CH_2]_3CC_2H_5$, $[CH_2$=$C(CH_3)C(O)O(C_3H_6O)_6]_2P(O)(OH)$ and combinations thereof in either the continuous or discontinuous phases of the emulsions. In the aqueous emulsions of the present invention where the network composition is in the discontinuous phase, the continuous phase comprises water. In the aqueous emulsions of the present invention where the network composition is in the continuous phase, the discontinuous phase comprises water.

Another aspect of the invention is directed to a method for producing an aqueous emulsion having a discontinuous and a continuous phase wherein at least one of these phases comprises the network polymer compositions of the present invention and the other comprising water. Similarly, another aspect of the invention is directed to a non-aqueous emulsion having a discontinuous and a continuous phase wherein at least one of these phases comprises the network polymer compositions of the present invention and the other phase comprises non-aqueous hydroxylic organic solvent. The network composition of the emulsions can be preformed or the method can include the preparation of the network composition. When the network composition of the present invention is prepared the monomers described above are polymerized under free radical polymerization conditions. The polymerizations are conducted in various solvents using catalysts and temperatures known in the art for polymerizing acrylates.

Examples of solvents that can be used in the present method include but are not limited to silicone fluid, water, alcohol, ester, hydrocarbon fluid or organic oil. Examples of catalyst that can be used in the method of the present invention include but are not limited to free radical catalysts such as peroxides such as hydrogen peroxide, ammonium persulfate, potassium persulfate and the like. Organic peroxy catalysts, such as dialkyl peroxides, e.g., diisopropyl peroxide, dilauryl peroxide, di-t-butyl peroxide, dicumyl peroxide, alkyl hydrogen peroxides such as t-butyl hydrogen peroxide, t-amyl hydrogen peroxide, cumyl hydrogen peroxide, diacyl peroxide, for instance acetyl peroxide, lauroyl peroxide, benzoyl peroxide, peroxy ester such as ethyl peroxybenzoate, pavalate peroxide, the azo compounds such as 2-azobis(isobutyronitrile), 1-azobis(1-cyclohexanecarbonitrile) and the like and other free radical generating catalysts.

The network polymer composition may be further processed under low or high shear to adjust the viscosity and sensory feel of the composition. This may be achieved, for example, by subjecting the composition to a moderate to high shearing force. Optionally, one or more fluids may be added to the silicone composition prior to the shearing. The network polymer composition of the present invention may be in a gel form, which contains the polymer itself and the solvents. It can also be processed (i.e. evaporated) to remove part or all of the solvents.

Once the network composition is prepared it can be added to water of a non-aqueous hydroxylic organic solvent to make the emulsions of the present invention.

Still yet another embodiment of the present invention is directed to demulsifiers. Some examples of oil phases include halogenated or non-halogenated C2-C30 hydrocarbons, and more particularly, halogenated or non-halogenated ethenes, butadienes, pentanes, hexanes, heptanes, octanes, benzenes, toluene, ethylbenzenes, xylenes, naphthalene, cresols, naphtha, fats, lubrication oils, petroleum, gasoline, diesel fuel, crude oil, fuel oils, jet fuels, heating oils, cleaning oils, vegetable oils, mineral oils, and tar or bitumen derivatives.

Emulsions can create problems in many industrial applications because the emulsions often do not separate into the liquid components for a prolonged time. In this case typically chemical additives, so-called demulsifying agents, are added to initiate, accelerate and complete the separation process. Demulsifying agents break emulsions and mixtures of polar solutes like water, and non-polar solvents like oil.

Demulsifiers are used to separate emulsions into polar (typically water) and non-polar liquids by incorporating the demulsifying agent into the emulsion. Demulsifiers are known in the art and usually comprise blends of surface-active chemicals. Typical organic demulsifier structures include, but not limited to sulfonates, sulfosuccinates, polyol esters, polyester amines, polymeric elastomers, sulfated polyol ester, oxyalkylated phenolic resins, alkylphenol alkoxylates, amine alkoxylates, quaternary amines, ethoxylated amines, bisamides, polyalkylene glycols, polymerized polyols, resin esters, polyether polyols, resin alkoxylates, modified polyols, polyimine alkoxylates and diepoxides.

Typical silicone demulsifiers include, but not limited to copolymers of polydimethylsiloxanes and polyalkylane oxides (silicone polyethers), alkylsilicones and alkylsilicone polyethers, arylsilicones and arylsilicone polyethers, aralkylsilicones and aralkylsilicone polyethers, organosilanes, alkoxysilanes.

However, despite the large number of demulsifiers available on the market, it is not possible to break all of the occurring petroleum/water emulsions rapidly, safely, efficiently, and with small quantities of addition products.

The reaction products described in the present invention can be used as demulsifying agents alone or accompanied by additional silicone and/or organic demulsifiers and these components can be utilized in the form of a blend, a solution, a dispersion, or either an oil-in-water or a water-in-oil emulsion or microemulsion or the various demulsifying agents can be added separately. When applied in solution suitable solvents can be selected from linear or branched, cyclic or acyclic, saturated or unsaturated, aliphatic or aromatic hydrocarbons, alcohol, ketones, esters, ethers and their blends or whatever solvent is commonly used in the particular application.

When the organic and/or silicone demulsifier is included, the weight ratio of the compositions of the present invention to the organic and silicone demulsifier is typically in the range of about 100:1 to about 1:1000, more typically in the range of about 5:1 to about 1:200.

The method of separating emulsions comprises the incorporation of a demulsifying-effective amount of demulsifier into the emulsion, allowing the emulsion to separate into at least two phases and separating these at least two phases from each other. The incorporation of the demulsifier into the emulsion to be separated can be achieved by any method known in the art for integrally mixing the demulsifier with the emulsion. The mixing procedure can use, for example, standard mixers, high-speed mixers or blenders, or shakers. The temperature can be unadjusted within room temperature limits (~20-30° C.), or adjusted as required, for example, to 40-150° C. for a suitable amount of time.

A typical application of the compositions in the present invention is the separation of crude oil emulsions. During extraction and production of crude oil, water or brine gets emulsified into the crude oil yielding a water-in-oil emulsion, which can be unstabilized or stabilized by surface active materials, organic solids, such as asphaltenes and resins, or inorganic solids. This water-in-oil emulsion gives rise to several down-stream problems; corrosion during refinery processes and greater energy requirement to pump the more viscous emulsion are to name a few. Thus, demulsifiers are extensively used in the petroleum industry, to break water-in-oil and oil-in-water emulsions; and before transportation, refining or processing the water content of the crude oil has to be reduced to pipeline specification levels (typically less then 0.05-2%) and this is typically achieved by injecting demulsifiers into the well, into the crude oil stream, at the separation equipment or at any other suitable points.

The cross linked copolymers of the present invention will cause improved demulsifying action as demulsifying agents in the Mining and Petroleum Industry, both in the oil field and refineries, including, but not limited to desalters; bitumen extraction from oils sands (separating bitumen froth and solvent diluted bitumen emulsions); in the separation of waste oils, slop oils, sludges, such as oily waste from desalters, waste water skimmings, refinery and petrochemical plant waste (tank bottom washes, coker drum waste, "dirty bleeds" etc.), steel and aluminum industrial waste, including synthetic lubes, high lithium grease, lube oil from rollers, metalworking fluid waste and paper plant waste.

Dehazing (demulsification) of lubrication oils and lubrication oil waste, such as automotive waste (motor oil etc.), bunker oil are also possible applications of the reaction products in the present invention.

Another typical industrial use of the reaction products in the present invention is diesel fuel (including bio-diesel) dehazing when the demulsifier eliminates small amount of emulsified water from the diesel fuel and diesel fuel antifoaming. The reaction product of the present invention will improve ore recovery from mining operations. The addition of the present invention to mining processes such as flocculation, separation, purification, concentration, and leaching and chemical extraction improves the separation of minerals from their gangue. Further applications of the emulsions comprising the copolymers of the present invention in oil and gas include separating asphaltene dispersants and drag reduction.

In the specification and claims herein, the following terms and expressions are to be understood as indicated.

The expression "hydrocarbon radicals" means any hydrocarbon group from which one or more hydrogen atoms has been removed and is inclusive of alkyl, alkenyl, alkynyl, cyclic alkyl, cyclic alkenyl, cyclic alkynyl, aryl, aralkyl and arenyl and may contain heteroatoms.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

Other than in the working examples or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges. As used herein, integer values of stoichiometric subscripts refer to molecular species and non-integer values of stoichiometric subscripts refer to a mixture of molecular species on a molecular weight average basis, a number average basis or a mole fraction basis. In the case of mixtures of the compounds of the present invention, it should be readily apparent that the stoichiometric subscripts of mixtures would have average values for the subscripts that may be either integral or non-integral in contrast to those of pure compounds.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The term "cross-linked polymers" means polymer molecules which are built from monomers which are linked together at many points other than their ends and as a result molecules with large size form and the material is non-pourable solid or gel-like which cannot be dissolved in any solvent. Cross-links are bonds that link one polymer chain to another. They can be covalent bonds or ionic bonds. "Polymer chains" can refer to synthetic polymers or natural polymers. In synthetic polymers, crosslinking refers to the use of crosslinks to promote a difference in the polymers' physical properties.

The copolymers in our invention are "non-crosslinked", which means that their monomers are either not linked together at points other than their ends or the linkages between the polymers are so few that the copolymer is either liquid or can be dissolved in at least one solvent.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the present invention as a reaction product of initial materials reference is made to the initial species recited and it is to be noted that additional materials may be added to the initial mixture of synthetic precursors. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example finely divided solids such as pigments may be dispersed into the reaction mixture, before during or after reaction to produce a reaction product composition that additionally comprises the non-reactive component, e.g. a pigment. Additional reactive components may also be added; such components may react with the initial reactants or they may react with the reaction product; the phrase "reaction product" is intended to include those possibilities as well as including the addition of non-reactive components.

Other optional ingredients may be added in the compositions of the present invention including coupling agents, e.g., silane coupling agents, curing aids, e.g., including activators, retarders and accelerators, processing additives such as oils, plasticizers, tackifying resins, silicas, other fillers, pigments, fatty acids, zinc oxide, waxes, antioxidants and anti-ozonants, peptizing agents, reinforcing materials such as, for example, carbon black, and so forth. Such additives are selected based upon the intended use and such selection is within the knowledge of one of skill in the art, as are the required amounts of such additives known to one of skill in the art.

Other embodiments of the invention will be apparent to those skilled in the art from a consideration of this specification or practice of the invention disclosed herein. It is intended that the specification and examples be considered as exemplary only, with the true scope and spirit of the invention being defined by the following claims.

The compositions of the present invention can be used commercially as a demulsifying agents, in agricultural compositions including fertilizers, in cosmetics and personal care products, in household cleaners, in coating compositions such as waxes and the like, in water processing apparatuses as well as other products.

As used herein the term "non-aqueous hydroxylic organic compound" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

SYNTHETIC EXAMPLES

Example 1

Preparation Network Polymer Composition 1

Mixture through 1 through 4 in Table I were used to prepare Network Polymer Composition I. Mixer 1 was placed in a 2 L IRA mixer. Nitrogen was bubbled through for 30 minutes to remove oxygen from the system. The mixture was heated to 55° C. under nitrogen and held at the temperature. Mixture 2 and mixture 3 were added over a 5-minute time period. The mixture was cooled to 25 C after two hours. Mixture 4 was then added and the mixture was mixed for 30 minutes to give an off-white soft solid.

TABLE I

| INGREDIENTS | WEIGHT (grams) |
|---|---|
| Mixture 1 | |
| Trimethylolpropane trimethacrylate | 0.2 |
| Acrylic acid | 3.9 |
| Phosphate mono-ester of polypropylene glycol mono-methacrylate (MW = 500) | 151.2 |
| Phosphate di-ester of polypropylene glycol mono-methacrylate (MW = 900) | 15.4 |
| Polyproplyeneglycol mono-methacrylate (MW = 400) | 8.4 |
| Tergital TMN-6* | 7.0 |
| Water | 443.8 |
| Sodium hydroxide solution (40 wt % in water) | 39.7 |
| Mixture 2 | |
| Sodium bisulfite solution (10% in water) | 1.8 |
| Ferrous ammonium sulfate solution (0.2% in water) | 3.5 |

TABLE I-continued

| INGREDIENTS | WEIGHT (grams) |
| --- | --- |
| Mixture 3 | |
| Potassium persulfate solution (4.5 wt % in water) | 21.0 |
| Mixture 4 | |
| Sodium metabisulfite solution (10 wt % in water) | 35.0 |

*Tergital TMN-6 is a Branched Secondary Alcohol Ethoxylates, available at Dow Chemicals.

Example 2

Preparation of Network Polymer Composition II

Mixture 1 through 4 in Table II were used to prepare Network Polymer Composition I. Mixer 1 was placed in a 2 L IRA mixer. Nitrogen was bubbled through for 30 minutes to remove oxygen from the system. The mixture was heated to 55° C. under nitrogen and held at the temperature. Mixture 2 and mixture 3 were added over a 5-minute time period. The mixture was cooled to 25° C. after two hours. Mixture 4 was then added and the mixture was mixed for 30 minutes to give an off-white soft solid.

TABLE II

| INGREDIENTS | WEIGHT (grams) |
| --- | --- |
| Mixture 1 | |
| Phosphate mono-ester of polypropylene glycol mono-methacrylate (MW = 500) | 108.0 |
| Phosphate di-ester of polypropylene glycol mono-methacrylate (MW = 900) | 11.0 |
| Polyproplyeneglycol mono-methacrylate (MW = 400) | 6.0 |
| Tergital TMN-6* | 5.0 |
| Sag 330** | 0.3 |
| Water | 314.7 |
| Sodium hydroxide solution (40 wt % in water) | 28.4 |
| Mixture 2 | |
| Sodium bisulfite solution (10% in water) | 1.3 |
| Ferrous ammonium sulfate solution (0.2% in water) | 2.5 |
| Mixture 3 | |
| Potassium persulfate solution (4.5 wt % in water) | 15.0 |
| Mixture 4 | |
| Sodium metabisulfite solution (10 wt % in water) | 25.0 |

*Tergital TMN-6 is a Branched Secondary Alcohol Ethoxylates, available at Dow Chemicals.
**Sag 330 is a silicone-based antifoam emulsion, available at Momentive Performance Materials.

Example 3

Preparation of Network Polymer Composition III

Part 1 through 3 in Table III were used to prepare Network Polymer Composition III. The ingredients in Part 1 were placed mixed under nitrogen. Nitrogen was bubbled for 30 minutes to remove oxygen from the system. The mixture was heated to 50° C. and held at that temperature. Part 2 and Part 3 were added into Part 1 at 50° C. The mixture was heated at 55° C. for approximated three hours to give an off-white soft solid.

TABLE III

| INGREDIENTS | WEIGHT (grams) |
| --- | --- |
| Part 1 | |
| Phosphate mono-ester of polypropylene glycol mono-methacrylate (MW = 500) | 25.9 |
| Phosphate di-ester of polypropylene glycol mono-methacrylate (MW = 900) | 2.6 |
| Polyproplyeneglycol mono-methacrylate (MW = 400) | 1.4 |
| Water | 70.0 |
| Sodium hydroxide solution (40 wt % in water) | q.s. to pH 5 |
| Part 2 | |
| Sodium bisulfite | 0.15 |
| Part 3 | |
| Potassium persulfate | 0.3 |

Example 4

Preparation of Network Polymer Composition IV

Part 1 through 3 in Table IV were used to prepare Network Polymer Composition IV. The ingredients in Part 1 were placed mixed under nitrogen. Nitrogen was bubbled for 30 minutes to remove oxygen from the system. The mixture was heated to 50° C. and held at that temperature. Part 2 and Part 3 were added into Part 1 at 50° C. The mixture was heated at 55° C. for approximated three hours to give an off-white soft solid.

TABLE IV

| INGREDIENTS | WEIGHT (grams) |
| --- | --- |
| Part 1 | |
| Polyethyleneglycol diacrylate | 0.08 |
| Acrylic acid | 0.55 |
| Phosphate mono-ester of polypropylene glycol mono-methacrylate (MW = 500) | 21.6 |
| Phosphate di-ester of polypropylene glycol mono-methacrylate (MW = 900) | 2.2 |
| Polyproplyeneglycol mono-methacrylate (MW = 400) | 1.2 |
| Water | 74.4 |
| Sodium hydroxide solution (40 wt % in water) | q.s. to pH 5 |
| Part 2 | |
| Sodium bisulfite | 0.15 |
| Part 3 | |
| Potassium persulfate | 0.3 |

Example 5

Preparation of Network Polymer Composition V

Part 1 through 3 in Table V were used to prepare Network Polymer Composition V. The ingredients in Part 1 were placed mixed under nitrogen. Nitrogen was bubbled for 30 minutes to remove oxygen from the system. The mixture was heated to 50° C. and held at that temperature. Part 2 and Part 3 were added into Part 1 at 50° C. The mixture was heated at 55° C. for approximated three hours to give an off-white soft solid.

TABLE V

| INGREDIENTS | WEIGHT (grams) |
|---|---|
| Part 1 | |
| Acrylic acid | 0.55 |
| Phosphate mono-ester of polypropylene glycol mono-methacrylate (MW = 500) | 21.6 |
| Phosphate di-ester of polypropylene glycol mono-methacrylate (MW = 900) | 2.2 |
| Polyproplyeneglycol mono-methacrylate (MW = 400) | 1.2 |
| Water | 74.4 |
| Sodium hydroxide solution (40 wt % in water) | q.s. to pH 5 |
| Part 2 | |
| Sodium bisulfite solution | 0.15 |
| Part 3 | |
| Potassium persulfate | 0.3 |

Example 6

Use of Network Polymer Composition I as an Aqueous Phase Thickener

The thickened aqueous compositions of Example 6 were made by combining the listed ingredients in the relative amounts set forth in Table VI, according to the following procedures. Network Polymer Composition I prepared according to Example 1 was missed with D.I. water using an overhead mixer at 700 RPM for 10 minutes. The viscosities of the resulting materials (measured after 24 hours) are listed in Table VI.

TABLE VI

| | Sample 6-1 | Sample 6-2 | Sample 6-3 | Sample 6-4 |
|---|---|---|---|---|
| Ingredients | | | | |
| Network polymer composition I (grams) | 8.3 | 10 | 11.7 | 13.3 |
| Water (grams) | 41.7 | 40 | 38.3 | 36.7 |
| Property | | | | |
| Viscosity (cPs) | 4000 | 15000 | 128000 | 216500 |

Example 7

Use of Network Polymer Composition II as an Aqueous Phase Thickener

The thickened aqueous compositions of Example 7 were made by combining the listed ingredients in the relative amounts set forth in Table VII, according to the following procedures. Network Polymer Composition II prepared according to Example 2 was missed with D.I. water using an overhead mixer at 700 RPM for 10 minutes. The viscosities of the resulting materials (measured after 24 hours) are listed in Table VII.

TABLE VII

| | Sample 7-1 | Sample 7-2 | Sample 7-3 | Sample 7-4 |
|---|---|---|---|---|
| Ingredients | | | | |
| Network polymer composition II (grams) | 7.1 | 8.3 | 10 | 12.5 |
| Water (grams) | 42.9 | 41.7 | 40 | 37.5 |
| Property | | | | |
| Viscosity (cPs) | 22000 | 40500 | 71000 | 105500 |

Example 8

Use of Network Polymer Composition III, IV and V as Aqueous Phase Thickeners

The thickened aqueous compositions of Example 8 were made by combining the listed ingredients in the relative amounts set forth in Table VIII, according to the following procedures. Network Polymer Composition III, IV and V were prepared according to Example 3, 4 and 5 respectively. The ingredients were mixed using an overhead mixer at 700 RPM for 10 minutes. The viscosities of the resulting materials (measured after 24 hours) are listed in Table VIII.

TABLE VIII

| | Sample 8-1 | Sample 8-2 | Sample 8-3 |
|---|---|---|---|
| Ingredients | | | |
| Network polymer composition III (grams) | 16.7 | | |
| Network polymer composition IV (grams) | | 16.7 | |
| Network polymer composition V (grams) | | | 16.7 |
| Water (grams) | 83.3 | 83.3 | 83.3 |
| Property | | | |
| Viscosity (cPs) | 69000 | 75500 | 65000 |

Example 9

Use of Network Polymer Composition II as an Aqueous Phase Thickener

The thickened aqueous compositions of Example 9 were made by combining the listed ingredients in the relative amounts set forth in Table IX, according to the following procedures. Network Polymer Composition II prepared according to Example 2 was missed with D.I. water using an overhead mixer at 700 RPM for 10 minutes. The viscosities of the resulting materials (measured after 24 hours) are listed in Table IX.

TABLE IX

| | Sample 10 |
|---|---|
| Ingredients | |
| Network polymer composition II (grams) | 20 |
| Water (grams) | 80 |

TABLE IX-continued

| Property | Sample 10 |
|---|---|
| Viscosity at pH 4 (cPs) | 67500 |
| Viscosity at pH 5 (cPs) | 69000 |
| Viscosity at pH 6 (cPs) | 70500 |
| Viscosity at pH 7 (cPs) | 79000 |
| Viscosity at pH 9 (cPs) | 84000 |

Example 10

Use of Network Polymer Composition II as an Aqueous Phase Thickener

The thickened aqueous compositions of Example 10 were made by combining the listed ingredients in the relative amounts set forth in Table X, according to the following procedures. Network Polymer Composition I prepared according to Example 2 was missed with D.I. water using an overhead mixer at 700 RPM for 10 minutes. pH was adjusted by using glycolic acid. The viscosities of the resulting materials (measured after 24 hours) are listed in Table X. Network Polymer Composition II provided effective thickening of the aqueous solution in the range of pH 4-9.

TABLE X

| | Sample 10 |
|---|---|
| Ingredients | |
| Network polymer composition II (grams) | 20 |
| Water (grams) | 80 |
| Property | |
| Viscosity at pH 4 (cPs) | 67500 |
| Viscosity at pH 5 (cPs) | 69000 |
| Viscosity at pH 6 (cPs) | 70500 |
| Viscosity at pH 7 (cPs) | 79000 |
| Viscosity at pH 9 (cPs) | 84000 |

Example 11

Use of Network Polymer Compositions I-V in Moisturizer Compositions

The moisturizing formulations of Example 11 were made by combining the listed ingredients in the relative amounts set forth in Table XI, according to the following procedures. Network Polymer Composition I-V were prepared according to Example 1-5 respectively. The ingredients were mixed using an overhead mixer at 700 RPM for 10 minutes. Panel tests showed that Sample 11-2 to 11-5, when applied on skin, provided significantly lower tack, lighter and more cushioning feel than Comparative Sample 11.

TABLE XI

| Ingredients | Sample 11-1 | Sample 11-2 | Sample 11-3 | Sample 11-4 | Sample 11-5 | Comparative Sample 11 |
|---|---|---|---|---|---|---|
| Network polymer composition I (grams) | 15 | | | | | |
| Network polymer composition II (grams) | | 15 | | | | |
| Network polymer composition III (grams) | | | 15 | | | |
| Network polymer composition IV (grams) | | | | 15 | | |
| Network polymer composition V (grams) | | | | | 15 | |
| Hispagel 200* | | | | | | 15 |
| Glycerin | 20 | 20 | 20 | 20 | 20 | 20 |
| Water (grams) | 65 | 65 | 65 | 65 | 65 | 65 |

*Hispagel 200 is a glycerin/glyceryl polyacrylate, available at Cognis.

Example 12

Use of Network Polymer Compositions I in a Sunscreen Lotion Composition

The sunscreen lotion compositions in Example 12 were made by combining the ingredients listed in Table XII, according to the following procedure: (1) Part A was made by mixing all the ingredients using an overhead mixer at 700 RPM until uniform; (2) Part B was mixed in a separate container and then added to Part A; (3) the mixture was then mixed until uniform. Stable o/w emulsions were prepared. Sample 12 provided a lighter and silkier feel than Comparative Sample 12. It also exhibited lower tack.

TABLE XII

| Ingredients | Sample 12 Weight (grams) | Comparative Sample 12 Weight (grams) |
|---|---|---|
| Part A | | |
| Network polymer composition I | 8 | |
| Pemulen TR-2* | | 0.2 |
| Water | 26 | 33.8 |
| Glycerin | 2 | 2 |
| Part B | | |
| Octyl methoxycinnamate | 3 | 3 |
| Octyl salicylate | 1 | 1 |

*Pemulen TR-2 is an Acrylates/C10-30 Alkyl Acrylate Crosspolymer, available at Lubrizol.

Example 13

Use of Network Polymer Compositions I in a Color Cosmetic Composition

The color cosmetic compositions in Example 13 were made by combining the ingredients listed in Table XIII and mixing using an overhead mixer until uniform. Panel test showed that Sample 13, when applied on skin, exhibited better spreading and sensory than Comparative Example 13.

TABLE XIII

| Ingredients Part A | Sample 13 Weight (grams) | Comparative Sample 13 Weight (grams) |
|---|---|---|
| Network polymer composition I | 20 | |
| Hispagel 200* | | 20 |
| Water | 77 | 77 |
| Aeroxide TiO₂ P25** | 3 | 3 |

*Hispagel 200 is a glycerin/glyceryl polyacrylate, available at Cognis.
**Aeroxide TiO$_2$ P25 is a titanium dioxide, available at Evonik Degussa.

Example 14

Use of Network Polymer Compositions I in a Rinse-Off Hair Conditioner Composition The rinse-off hair conditioner compositions of Sample 14 and Comparative Example 14 were made by combining the ingredients listed in Table XIV, according to the following procedure: (1) Part A was made by combining the ingredients and mixing at 60° C. until uniform; (2) Part B was mixed in a separate container and then added to Part A; (3) the mixture was then mixed until uniform. Panel tests showed that Network Polymer Composition I improved the softness and sleekness of the hair.

TABLE XIV

| Ingredients | Sample 14 Weight (grams) | Comparative Sample 14 Weight (grams) |
|---|---|---|
| Part A | | |
| Network polymer composition I | 25.5 | 0 |
| SF1632* | 5 | 5 |
| D.I. water | 59.5 | 85 |
| Tergital TMN-6** | 0.1 | 0.1 |
| Part B | | |
| D.I. water | 9.8 | 9.8 |
| Polyquaternium-10 (Ucare polymer JR30M) | 1 | 1 |

*SF1632-C16-18 alkyl dimethicone, available at GE silicones; and Polyquaternium-10 UCARE polymer JR30M, available at Dow Chemicals.
**Tergital TMN-6 is a Branched Secondary Alcohol Ethoxylates, available at Dow Chemicals;

Example 15

Preparation of Network Polymer Composition XV

Mixture 1 through 4 in Table XV were used to prepare Network Polymer Composition I. Mixture 1 was placed in a 2 L mixer. Nitrogen was bubbled through for 30 minutes to remove oxygen from the system. The mixture was heated to 55° C. under nitrogen and held at the temperature. Mixture 2 and mixture 3 were added over a 5-minute time period. The mixture was cooled to 25° C. after two hours. Mixture 4 was then added and the mixture was mixed for 30 minutes to give an off-white soft solid. The soft solids were then mixed with acetone in 1:4 weight ratios for 30 minutes. The mixture was allowed to settle for 30 minutes. The liquid layer was then decanted. The solids were dried in a vacuum oven at 80° C. for two hours and then grinded with a coffee grinder to obtain a white powder.

TABLE XV

| INGREDIENTS | WEIGHT (grams) |
|---|---|
| Mixture 1 | |
| Acrylic acid | 2.8 |
| Phosphoric acid mono-ester of polypropylene glycol mono-methacrylate (MW = 500) | 108.0 |
| Phosphoric acid di-ester of polypropylene glycol mono-methacrylate (MW = 900) | 11.0 |
| Polyproplyeneglycol mono-methacrylate (MW = 400) | 5.0 |
| Tergital TMN-6* | 5.0 |
| Water | 338.7 |
| Sodium hydroxide solution (40 wt % in water) | 28.4 |
| Mixture 2 | |
| Sodium bisulfite solution (10% in water) | 1.3 |
| Ferrous ammonium sulfate solution (0.2% in water) | 2.5 |
| Mixture 3 | |
| Potassium persulfate solution (4.5 wt % in water) | 15.0 |
| Mixture 4 | |
| Sodium metabisulfite solution (10 wt % in water) | 25.0 |

*Tergital TMN-6 is a Branched Secondary Alcohol Ethoxylates, available at Dow Chemicals.

Example 16

Use of Network Polymer Compositions XV in a Moisturizer Composition

The moisturizing formulations of Example 16 were made by combining the listed ingredients in the relative amounts set forth in Table XVI, according to the following procedures. Network Polymer Composition XV were prepared according to Example 15. The ingredients were mixed using Speed mixer at 3000 RPM for 2 minutes. Panel tests showed that Sample 16, when applied on skin, provided lower after-rub-in tack and more cushioning feel than Comparative Sample 16-1. Comparative sample 16-2 was not a stable mixture.

TABLE XVI

| Ingredients | Sample 16 Weight (grams) | Comparative Sample 16A Weight (grams) | Comparative Sample 16B Weight (grams) |
|---|---|---|---|
| Network polymer composition XV | 0.5 | 0.5 | 0 |
| Glycerin | 1 | 1 | 1 |
| D.I. water | 7 | 8.5 | 7.5 |
| Velvesil 125* | 1.5 | 0 | 1 |

*Velvesil 125 is a silicone gel product, available at Momentive Performance Materials.

Results:
Result Summary:
Examples 1-5, 15 presented six synthesis examples, each representing a different structure. Examples 6-10 showed how these polymer network compositions thickened water at different solids levels or pH. Example 11 proved that the polymer network composition of the present invention could significantly improve the sensory of a moisturizer formulation, compared with Hispagel 2000, a benchmark product. In Example 12, the polymer network composition showed to provide a lighter, silkier sensory in a sunscreen formulation, as well as oil-in-water emulsifying capability. Example 13 showed that the polymer could help to disperse hydrophilic pigment in a color cosmetic formulation. Example 14 showed that this polymer network composition could bring the softness and sleekness feels to hair when incorporated in a rinse-off hair conditioner formulation. Example 15 showed a synergistic effect between the present structure and a silicone gel.

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Other embodiments of the invention will be apparent to those skilled in the art from a consideration of this specification or practice of the invention disclosed herein. It is intended that the specification and examples be considered as exemplary only, with the true scope and spirit of the invention being defined by the following claims.

What is claimed is:

1. An aqueous emulsion having a continuous and a discontinuous phase wherein said discontinuous phase comprises either water or comprises a network copolymer composition comprising a reaction product of:
   i) at least one anionic polymerizable ethylenically unsaturated monomer (I) selected from the group consisting of

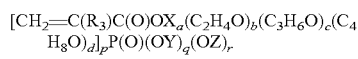

where
   $R_3$=H or alkyl of 1 to about 6 carbon atoms;
   X=alkyl, aryl, or alkaryl &radical connecting group of 0 to about 9 carbon atoms;
   a is 0 to about 100;
   b is 0 to about 100;
   c is 2 to about 100;
   d is 0 to about 100;
   q is 0 to about 2;
   r is 0 to about 2;
   p is 1 to about 3 subject to the limitation that p+q+r=3; and
   Y and Z is H, or metal ion;
   and $$CH_2=C(R_3)C(O)OX_{a'}(C_2H_4O)_{b'}(C_3H_6O)_{c'}(C_4H_8O)_{d'}-SO_3-Y$$

where
   $R_3$=H or alkyl of from 1 to about 6 carbon atoms;
   X=alkyl, aryl, or alkaryl &radical connecting group of 0 to about atoms;
   a' is 0 to about 100;
   b' is 0 to about 100;
   c' is 2 to about 100;
   d' is 0 to about 100;
   Y is H, or metal ion; and
   (ii) one or more additional monomers (II) selected from the group consisting of acrylic acid/acrylate, methacrylic acid/methacrylate, acrylamides, vinyl acetate and styrene, which are copolymerizable with (I); and
   (iii) a cross-linking agent (III), capable of copolymerizing with (I) and (II), providing that when said network copolymer composition is in the discontinuous phase of said aqueous emulsion, water is in said continuous phase of said emulsion and when said network copolymer composition is in the continuous phase of said aqueous emulsion, water is in said discontinuous phase of said emulsion, wherein said network composition comprises from 70 to 99 weight percent of the at least one anionic polymerizable ethylenically unsaturated monomer (I) based on the total weight of the monomers.

2. The aqueous emulsion composition of claim 1 wherein said network composition comprises about 80 to about 99 weight percent based on the total weight of the monomers of said at least one anionic polymerizable ethylenically unsaturated monomer (I), about 0.5 to about 50 weight percent based on the total weight of the monomers of said additional monomers and about 0.1 to about 10 weight percent based on the total weight of the monomers of said cross-linking agent.

3. The aqueous emulsion of claim 1 wherein said monomer (I) is selected from the group consisting of $CH_2=C(CH_3)C(O)O(C_3H_6O)_6P(O)(OH)(ONa)$, $CH_2=C(CH_3)C(O)O(C_3H_6O)_6P(O)(OH)_2$ and $CH_2=CHC(O)O(C_3H_6O)_6P(O)(OH)(OH)_2$;
   said additional monomers (II) are selected from the group consisting of: $CH_2=CHC(O)OH$ and $CH_2=C(CH_3)C(O)O(C_3H_6O)_6H$; and
   said cross-linking agent (III) is selected from the group consisting of $[CH_2=C(CH_3)CO_2CH_2]_3CC_2H_5$ and $[CH_2=C(CH_3)C(O)O(C_3H_6O)_6]_2P(O)(OH)$.

4. The aqueous emulsion of claim 1 wherein a, b, d, a', b', and d' are each independently 0 to about 50 and c and c' are each independently 2 to about 50.

5. The aqueous emulsion of claim 4 wherein a, b, d, a', b', and d' are each independently 0 to about 15 and c and c' are each independently 2 to about 15.

6. An aqueous emulsion having a continuous and a discontinuous phase wherein said discontinuous phase comprises either water or comprises a network copolymer composition comprising a reaction product of:
   i) at least one anionic polymerizable ethylenically unsaturated monomer (I) selected from the group consisting of

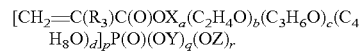

where
   $R_3$=H or alkyl of 1 to about 6 carbon atoms;
   X=alkyl, aryl, or alkaryl diradical connecting group of 0 to about 9 carbon atoms;
   a is 0 to about 100;
   b is 0 to about 100;
   c is 2 to about 100;
   d is 0 to about 100;
   q is 0 to 2;
   r is 0 to 2;
   p is 2 or 3 subject to the limitation that p+q+r=3; and
   Y and Z is H, or metal ion;
   and $$CH_2=C(R_3)C(O)OX_{a'}(C_2H_4O)_{b'}(C_3H_6O)_{c'}(C_4H_8O)_{d'}-SO_3-Y$$

where
   $R_3$=H or alkyl of from 1 to about 6 carbon atoms;
   X=alkyl, aryl, or alkaryl diradical connecting group of 0 to about 9 carbon atoms;
   a is 0 to about 100;
   b' is 0 to about 100;
   c' is 2 to about 100;
   d' is 0 to about 100;
   Y is H, or metal ion; and
   (ii) one or more additional monomers (II) selected from the group consisting of acrylic acid/acrylate, methacrylic acid/methacrylate, acrylamides, vinyl acetate and styrene, which are copolymerizable with (I), wherein said network composition comprises from 70 to 99 weight percent of the at least one anionic polymerizable ethylenically unsaturated monomer (I) based on the total weight of the monomers.

\* \* \* \* \*